United States Patent
Suzuki et al.

(10) Patent No.: US 6,248,968 B1
(45) Date of Patent: Jun. 19, 2001

(54) METHOD AND APPARATUS FOR ASSAYING SEEDS USED IN MEDICAL APPLICATIONS

(75) Inventors: Arata Suzuki, deceased, late of Ramsey, NJ (US), by Marcia Suzuki, legal representative; Mary Anne Dell, Pittsburgh, PA (US); James W. Gray, Charlotte, TN (US)

(73) Assignee: Capintec, Inc., Ramsey, NJ (US)

( * ) Notice: Subject to any disclaimer, the term of this patent is extended or adjusted under 35 U.S.C. 154(b) by 0 days.

(21) Appl. No.: 09/328,973

(22) Filed: Jun. 9, 1999

(51) Int. Cl.$^7$ ................ B07C 5/00; B07C 5/02
(52) U.S. Cl. .............. 209/576; 209/542; 209/544
(58) Field of Search ..................... 209/576, 589, 209/577, 578, 579, 580, 585, 586, 587, 588, 540, 542, 544

(56) References Cited

U.S. PATENT DOCUMENTS

| | | | |
|---|---|---|---|
| 4,144,970 | * | 3/1979 | McKnight et al. ........... 209/542 |
| 4,194,634 | * | 3/1980 | Kelly ........................... 209/589 |
| 4,372,941 | * | 2/1983 | Ryan ............................. 435/15 |
| 4,445,615 | * | 5/1984 | Bohme et al. ................ 209/555 |
| 5,076,502 | * | 12/1991 | Kitaguchi et al. ............ 241/36 |
| 6,106,455 | * | 8/2000 | Kan ................................. 600/7 |

FOREIGN PATENT DOCUMENTS

| | | | | |
|---|---|---|---|---|
| 1158748 | * | 12/1983 | (CA) | ........................ 209/576 |
| 2238537 | * | 2/1975 | (FR) | ........................ 209/576 |
| 594185 | * | 5/1959 | (IT) | ........................ 209/576 |
| 114180 | * | 5/1988 | (JP) | ........................ 209/576 |
| 10165575 | * | 6/1998 | (JP) | ........................ A63F/7/02 |

\* cited by examiner

Primary Examiner—Donald P. Walsh
Assistant Examiner—Daniel K. Schlak
(74) Attorney, Agent, or Firm—Martin Fleit

(57) ABSTRACT

A method and apparatus for assaying and sorting automatically a batch of radioactive seeds used in medical applications. The method and apparatus consist in feeding seeds from a vibratory feeder through a first gate to an EA measuring station where the equitorial anisotrophy of the seeds are determined. The seeds then pass automatically to a dose calibrator where their radioactivity level is determined. Based on the radiation measurements, a computer controls a turret wheel to position it correctly, to sort the seeds from the dose calibrator into a plurality of receptacles.

21 Claims, 8 Drawing Sheets

METHOD AND APPARATUS FOR ASSAYING SEEDS USED IN MEDICAL APPLICATIONS

FIELD OF THE INVENTION

The present invention relates to a method and apparatus for assaying radioactive seeds used in medical applications.

BACKGROUND OF THE INVENTION

Assaying of radioactive seeds is usually done by selecting a number of samples from a batch of seeds, and then checking each of the selected seeds for either or both of equatorial anisotropy (EA) and for level of radioactivity. This checking is performed manually by a person with the aid of conventional radiation counting equipment. Decisions concerning the suitability of the batch are made based on the samples tested. If there is a serious question concerning the batch, then each seed is individually manually tested. Each seed is a radioactive sealed source in the form of an elongated seed.

SUMMARY OF THE INVENTION

The object of the present invention is to provide a method and apparatus for automatically checking radioactive seeds in a batch to determine either or both EA and level of radioactivity, and then sorting the seeds according to the sensed assay information. In a specific embodiment, the method of the present invention includes the steps of feeding the seeds from a hopper one at a time (single file) along a conveying path in a fixed geometry, usually in the direction of their long axes. The seeds are moved to an EA measuring station, rotated in front of the EA test apparatus, moved to a dose calibration station, and based on nuclear count or radioactive activity, the seeds are moved to proper or preselected ones of a plurality of storage bins (up to 25), including a discard bin for seeds which are outside the specification range.

The foregoing method is accomplished by the present invention by apparatus including a storage bin to hold the seeds, and feeding the seeds by gravity out of the storage bin one at a time using a vibratory feeder, with or without an air assist to help fluidize the seeds. The seeds are introduced one at a time into a station for measuring EA. The feed into and out of the EA station is controlled by gates and photosensors, under the control of a microprocessor which also controls the vibratory feeder. EA measurements are taken by incrementally rotating an individual seed about its longitudinal axis. The incremental movement may be any preselected number of degrees of angular movement. Movements in the range of 30 to 60 degrees are preferred. At the end of each movement, a counting instrument takes a reading, which is fed to the microprocessor. At the end of the movements, that is when 360 degrees rotation has been effected, a decision is made whether to advance or discard the seed. If advanced, the seed feeds by gravity with or without an air assist, to the dose station. If discarded, the seed goes directly to a discard vial at the turret station. At this dose station, equipped with photosensors and gates, the level of radioactivity of the seed is measured. If the seed measures as having high activity, the seed is measured in both its 180 degree longitudinal orientations, to detect polar differences. The seed at the dose station is placed into, preferably lifted into, a radioactivity level counting instrument which feeds its output to the microprocessor. If the seed is not to be discarded, it is advanced to a turret wheel, provided with photosensors, which contains a plurality, 10–25, of receptacles, called pigs, and it is dropped via a funnel into the appropriate receptacle selected by the microprocessor based on the measurements taken for the particular seed. If discarded, the seed goes to a discard receptacle in the turret wheel. The apparatus is equipped with the appropriate motors, lift mechanism, photosensors, gates and controls.

Other and further objects and advantages of the present invention will become more readily apparent from the following detailed description of a preferred embodiment of the invention when taken in conjunction with the appended drawing.

DETAILED DESCRIPTION OF PREFERRED EMBODIMENT

Figure 1:
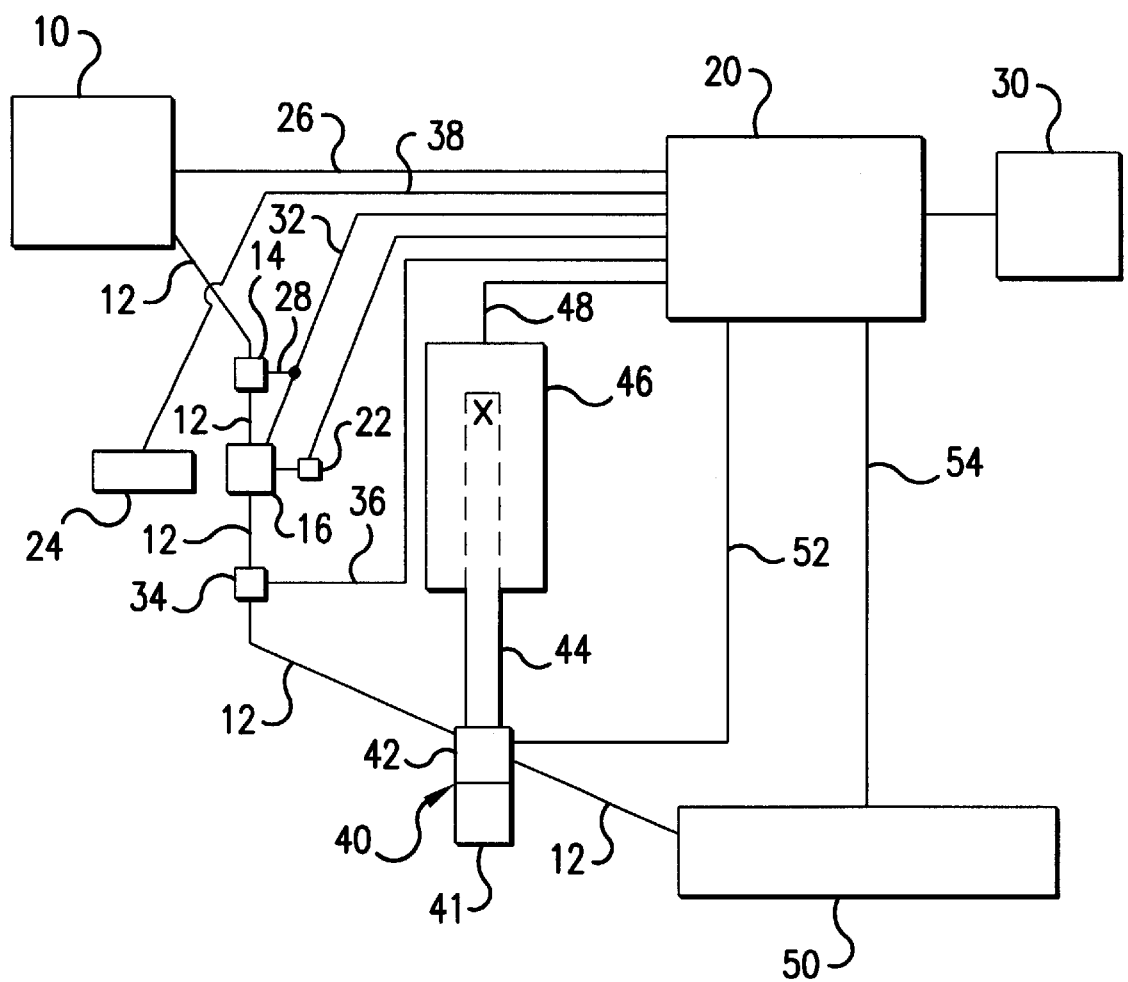
FIG. 1 is a block diagram of the novel method and apparatus of the present invention showing the automatic processing of a batch of radioactive seeds.

The novel method and apparatus is shown in block diagram in FIG. 1. As shown, the apparatus consists of a known vibratory feeder 10 that includes a storage bin to hold a batch of radioactive seeds, and to feed them one at a time with their major axes aligned with the feed path down a feed path or track 12. Feeding may be done in any known manner, but it is preferably done by gravity. An air input at the top of the track or path can be used to help fluidize the seeds, so that they move more smoothly. The track 12 has a V-shaped covered feeding groove that serves as the feed path. The seeds are advanced to a first gate 14 provided with a suitable photosensor to sense the presence of a queue of at least 4 seeds. The first gate may be of any known construction, such as for example the construction used for trapping seeds at the EA station, to be described subsequently, or may be a simple shutter that shuts off or opens the feed path under the control of a solenoid in a known manner. If a queue of 4 seeds is not sensed, then the microprocessor 20 via line 26 orders or commands the vibratory feeder 10 to feed additional seeds down track 12 until the queue reaches 4 in number. Alternatively, one photosensor can sense the presence of a seed in position at the gate to be fed to the EA station, and another photosensor can sense the queue of 4. The output of the photosensors is sent by line 28 to the microprocessor 20.

When the EA station 16 is available, the microprocessor 20 with display 30 commands the first gate 14 via line 32 to release one seed. The released seed then travels down the track by gravity, past another photosensor, to EA station 16 which is interposed into the path or track so that the track portion above the EA station 16 leads seeds to the EA station, and the track portion below the EA station 16 receives the seeds released by the EA station, and carries them on downstream. At the EA station 16, the seed is trapped and held in a predetermined orientation, preferably in a vertical or horizontal orientation. This can be accomplished by any known mechanism, such as, a shaft having a diametrical hole extending only partly through or using two horizontally disposed parallel-extending rollers with a gap less than the thickness or diameter of the seed shaft. If the mechanism is two rollers, a seed dropped onto the rollers can be easily rotated, and released by shifting one roller away from the other, or rotating the rollers to align with the downstream track portion. When using a shaft with the diametrical hole, the shaft is positioned with the hole opening facing up, and the seed is received in the hole for measurement. When measurement is completed under control of the microprocessor 20 and the seed is to be released, the shaft is rotated 180 degrees and the seed drops out and then, travels down by gravity continuing along the conveying track 12 past a photosensor 34 feeding its output via line 36 to the microprocessor 20. The air injected into the path or track 12 helps release the seed.

As shown in the block diagram of FIG. 1, the seed is held vertically in a separate block 16 which registers with the conveying track 12 top and bottom as described. The separate block 16 in the form of a cylinder is mounted for rotation about a vertical axis, and is driven in a conventional way by a suitable step motor 22, so the block can be rotated in 30–60 degree increments, preferably 45 degree increments, stopping after each incremental rotation for a measurement. A Beta C counter 24, such as, a Beta C Counter made by Capintec, Inc. of Ramsey, N.J., modified with a front window opening dimensioned to substantially match the profile of the portion of the rotating block holding the seed under measurement, is positioned adjacent the block trapping the seed to effect the radioactivity measurements. The counter contains a NaI scintillation crystal and a photomultipier tube with the necessary ancillary components to effect the measurement to evaluate EA. The output of the counter is fed via line 38 to the microprocessor 20 as shown.

When the EA measurement has been completed and the seed released, it travels down the track to the dose calibration station 40 where it is received in a mechanism 42 that can align the seed with its long axis coincident with a vertical tube 44 that extends up into dose calibrator 46 and terminates at a position X within the dose calibrator 46 at which a suitable measurement of radioactivity level can be taken. An instrument suitable for this purpose is the Capintec CRC712 dose calibrator which includes an ionization chamber and the necessary components to effect the radioactivity measurement. Output signals from the dose calibrator are fed via line 48 to the microprocessor 20. The seed to undergo testing is pushed up the tube to the measuring position, measured, withdrawn down the tube, rotated 180 degrees, if high activity is detected, and pushed up the tube, measured again, withdrawn down the tube, and released to the downstream track portion leading to the turret wheel or station 50. Any known lift mechanism can be used to effect the described movements under the control of the microprocessor 20 via line 52, and it can function mechanically, pneumatically, or hydraulically. The simplest mechanism is a spool shaft that is provided with a through diametrical hole. The upstream track portion couples to the dose station at a downward angle, about 45 degrees. When a seed is received in the through hole in the spool, the spool is rotated to orient the seed to the vertical, whereupon it registers with the vertical tube extending into the dose calibrator. The seed can now be pushed or lifted up the tube, such as pneumatically by pressurized air from below or by applying a vacuum from above, or both, and held in measuring position simply by maintaining the air pressure or vacuum, as the case may be. Unit 41 of dose calibrator station 40 provides this function. When the measurement is completed, the air pressure or vacuum is released or reversed whereupon the seed returns to the hole in the spool. The spool can now be shifted axially, rotated 180 degrees and shifted axially back to its initial position where the seed is aligned with and registers with the vertical tube. Once again the seed can be pushed or lifted up the tube to the measuring position, and another measurement taken. Now the air pressure or vacuum can be released or reversed and the seed falls back to the hole. Then the spool is shifted and rotated to align the seed with the exit from the dose station 40, which in turn aligns with the downstream track portion 12. The seed is now conveyed by gravity along track 12, with or without fluidizing air, to the turret wheel or station 50. The turret wheel 50, under the control of the microprocessor via line 54, is positioned at the correct angular position to present the correct receptacle to the discharge of the track portion 12 leading from the dose station 40.

Figure 3:
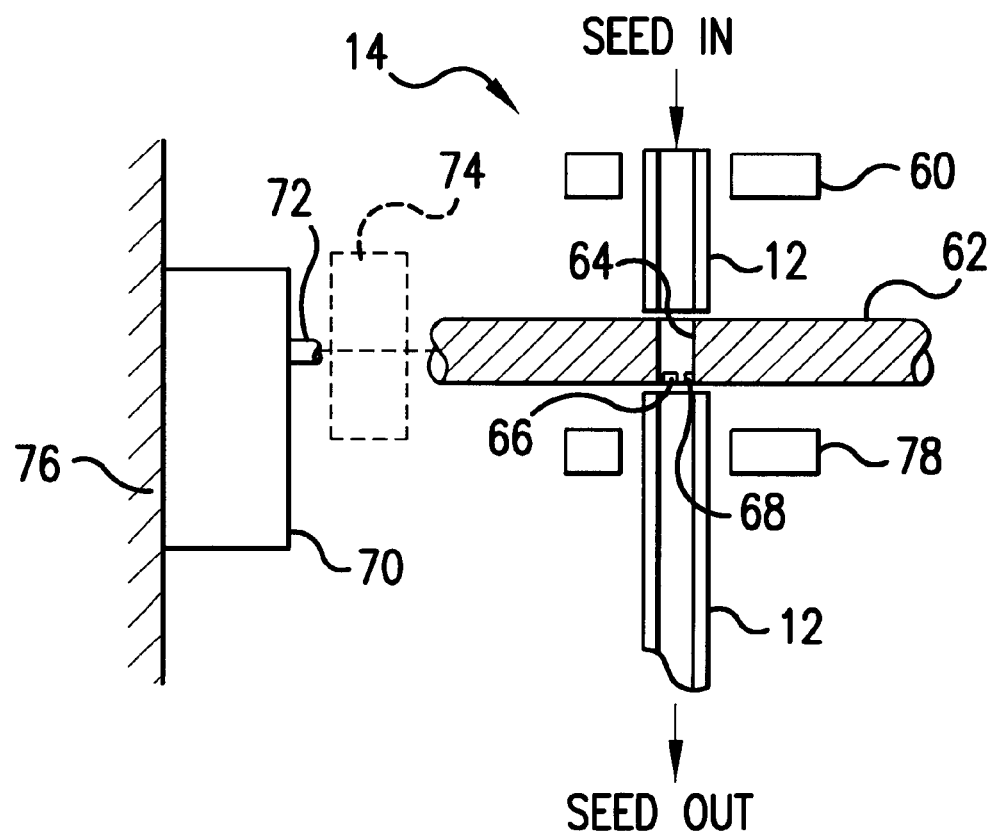
FIG. 3 is a schematic diagram of the first gate.
Figure 4:
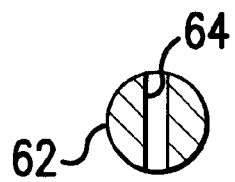
FIG. 4 is a section through the first gate showing the seed trap.

Referring now to FIGS. 3 and 4 the first gate is shown in more schematic detail. As shown, upstream seed track portion 12 is provided with a photosensor 60 just before entry into the gate 14. The gate 14 essentially consists of a shaft 62 with a diametrical hole 64 that has a narrowed section 66 with a central opening 68 at one end. The shaft is mounted in a conventional manner for rotation. The shaft 62 is rotated by a motor 70 whose output shaft 72 is mechanically coupled through a conventional mechanism 74 to drive the shaft 62. A frame portion 76 supports the motor 70. The downstream seed track 12 also has an associated photosensor 78. When a seed feeds down the upstream track portion 12, it is trapped in the hole 64 in shaft 62. To release the seed, the motor 70 rotates the shaft 62 180 degrees, whereupon the seed is discharged down into the downstream track 12.

Figure 5:
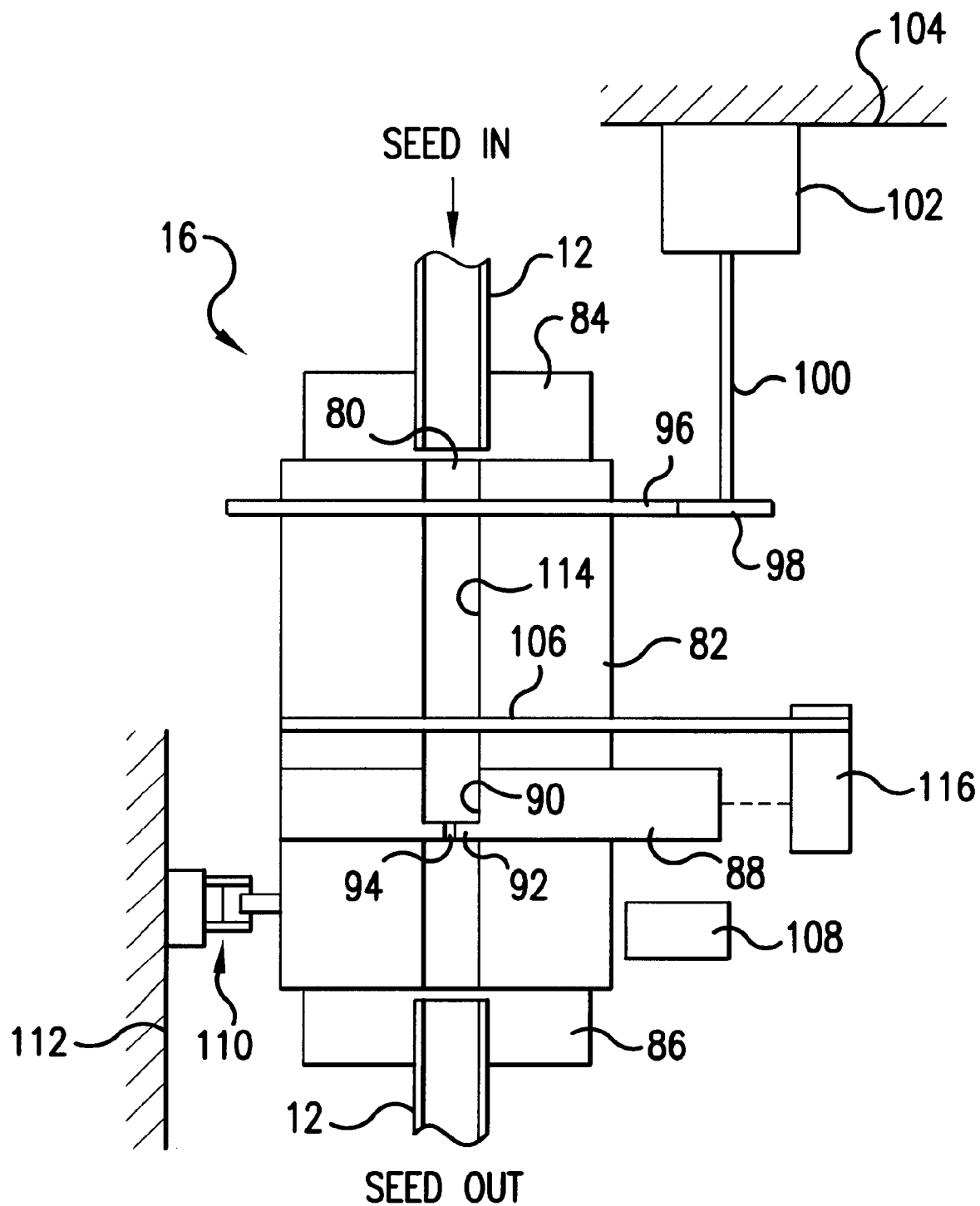
FIG. 5 is a schematic diagram of the EA station.

The EA station 16 is shown in FIG. 5, and consists of an upstream track section 12 which terminates facing down at the entrance 80 of station 16. A block 82, preferably cylindrical is bearing supported top and bottom by conventional bearings 84 and 86, so that block 82 can rotate. Block 82 has a vertical through hole 114 that matches the seed track dimensionally so a seed can pass through. A bore is cut in block 82 horizontally, and receives a shaft 88 having a hole like that of shaft 62. That is, a main hole 90 with narrowing 92 and central opening 94. The shaft 88 enables a seed to be trapped in the block 82 in the same manner as the function of the gate 14. While trapped, a seed can be rotated by the wheel or gear 96 fixed to block 88 which is driven via a wheel or gear 98 connected to the output drive shaft 100 of stepper motor 102 mounted to a frame portion 104. Suspended from the block 88 by a conventional bracket 106 is a driver 116 in the form of a motor or solenoid mechanically coupled to rotate the shaft 88 at the end of the measurement to release the seed. The lower end of the hole in the block 88 matches and registers with the downstream track portion 12. A photosensor 108 sits adjacent the lower end of the block 88 to sense passage of a seed. A conventional homing device 110, consisting of a pin fixed on block 88 and micro-switches mounted on a frame part 112 ensure that a full revolution is made during EA measurement.

Figure 6:
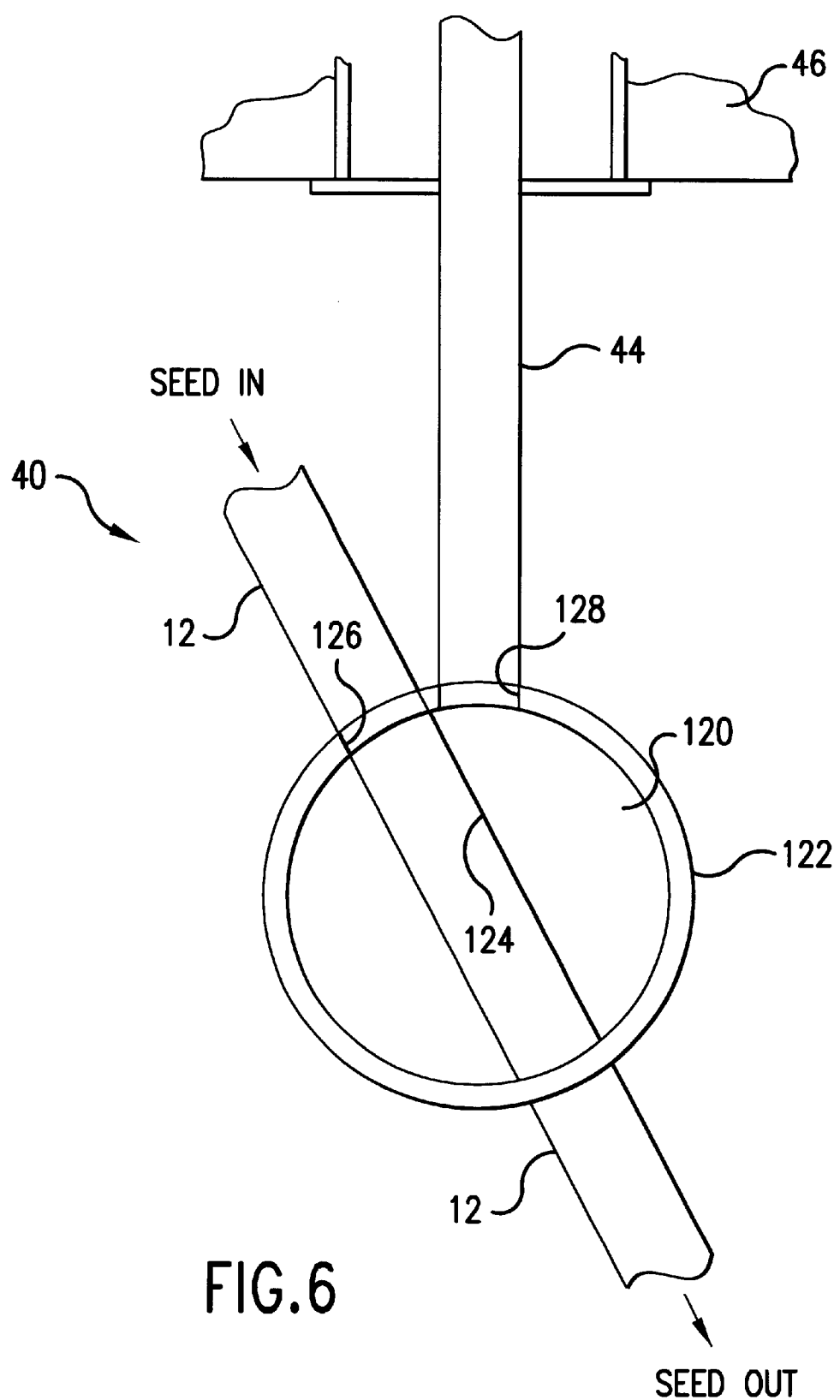
FIG. 6 is a schematic diagram of the dose calibrator station.
Figure 7:
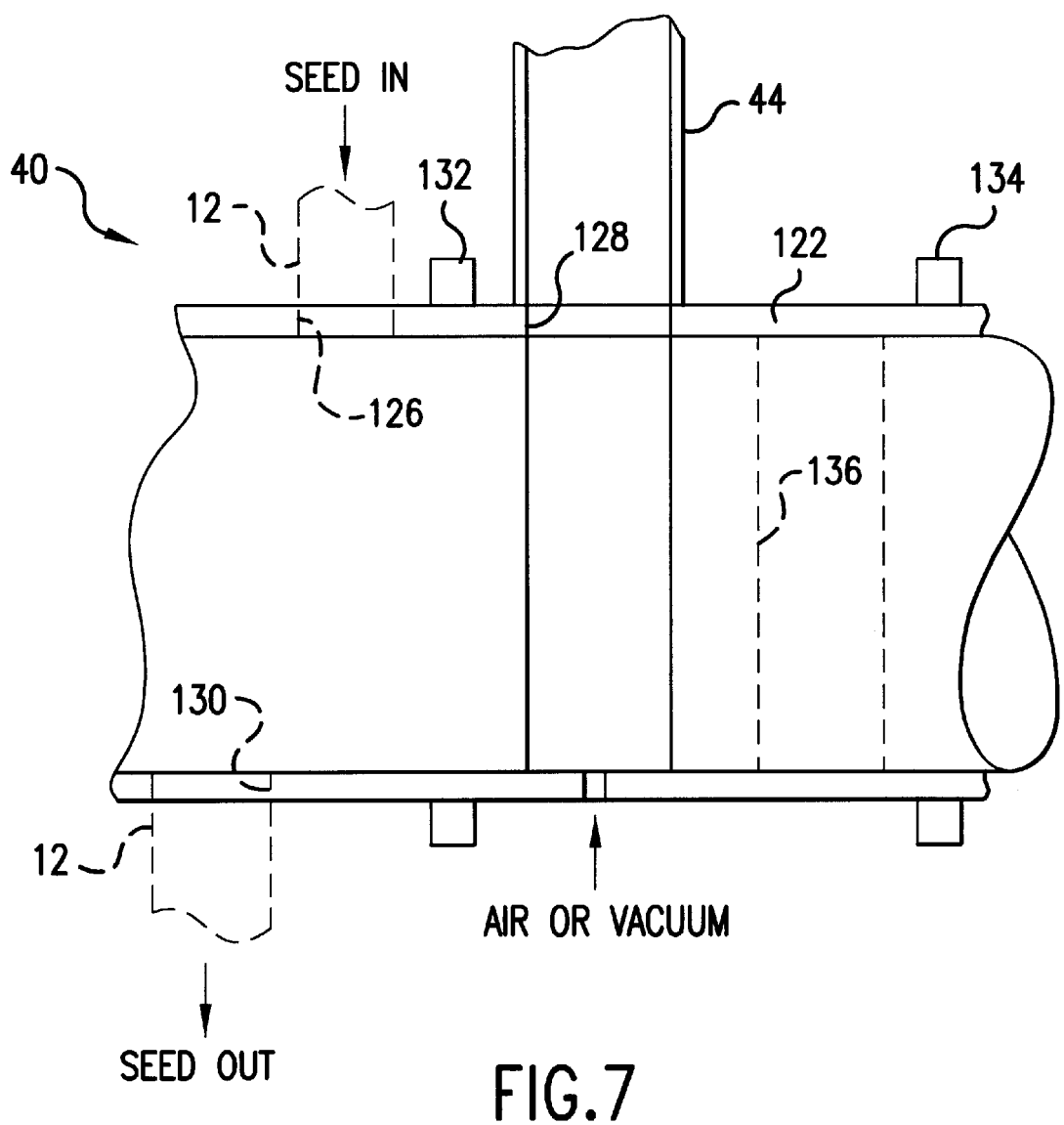
FIG. 7 is a schematic diagram showing the spool shaft of the dose calibrator station.

The dose calibrator station 40 is shown schematically in FIGS. 6 and 7, and consists of a spool shaft 120 which is mounted in a supporting cylinder 122 supported in turn on a frame part (not shown). The spool shaft has a through diametrical hole 124, and the supporting cylinder has three axially displaced openings 126, 128 and 130 all of which match the seed track dimensionally to enable passage of a seed. As shown in FIG. 6, the upstream seed track portion 12 is aligned with the opening 126 and the hole 124 so that a seed can pass into the hole 124 where it is trapped by the cylinder 122. The spool shaft 120 can now be shifted axially and rotated to align with the opening 128 and up tube 44 that leads into the dose calibrator 46. Bearing 132 and 134 provide the necessary support and enable shifting and rotation of the spool shaft 120. When the seed comes down, the spool shaft can now be shifted to the dotted line position 136 shown in FIG. 7 whereupon the spool shaft 120 can be rotated 180 degrees to invert the seed. Next, the shaft 120 is shifted axially to return to registry with opening 128 and up tube 44 to send the seed up the tube 44. When next the seed comes down, the shaft 120 can be shifted to the opening 130 which registers with the down track portion 12. An opening 134 in cylinder 122 enables pneumatic control of the seed in the hole 124 and its positioning and repositioning at the measuring point X within the dose calibrator 46. Photosensors can be associated with the dose calibration station 44 to detect arrival of a seed and exit of a seed.

Figure 8:
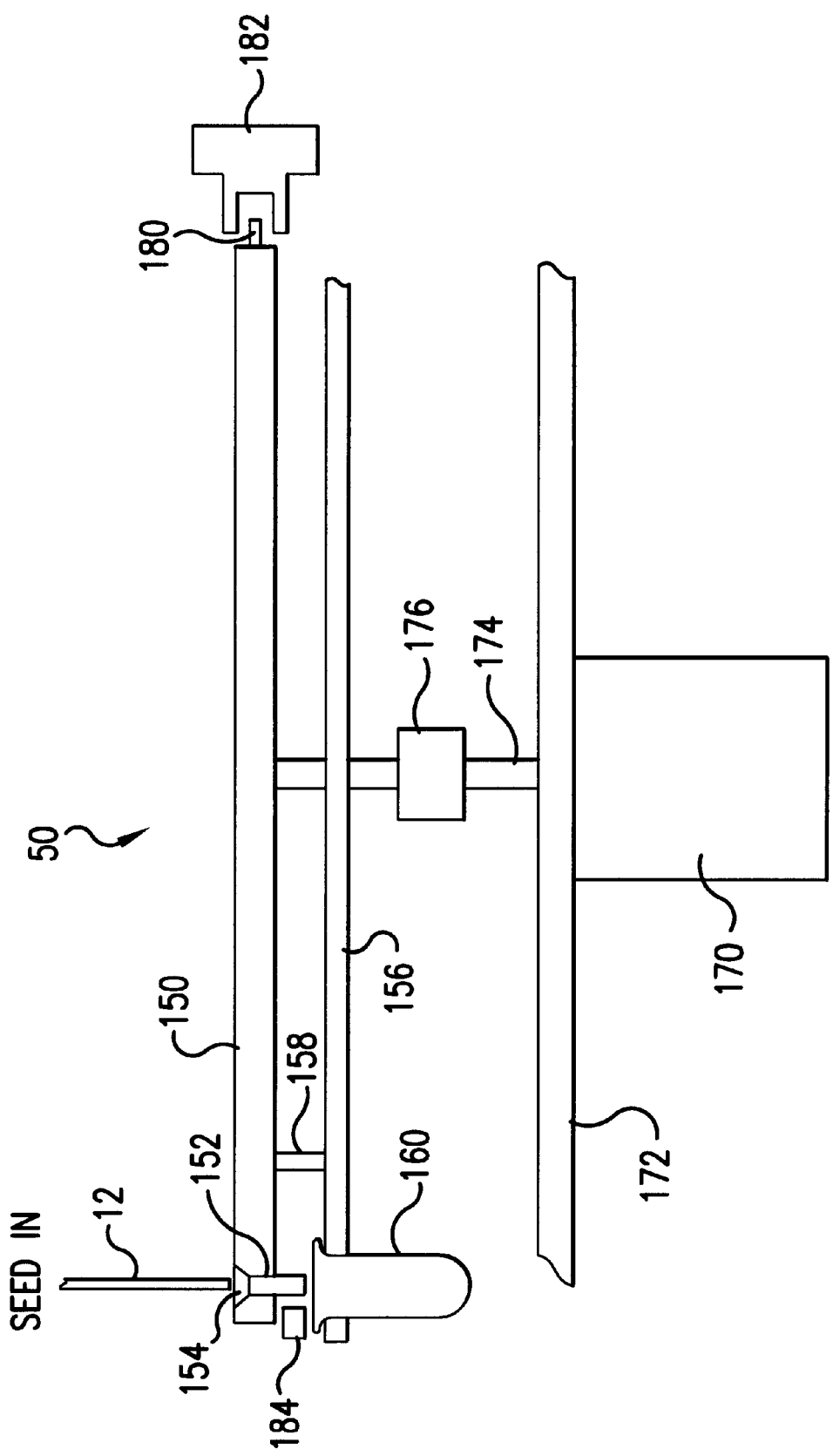
FIG. 8 is a schematic diagram showing the turret or sorting station.

The turret or sorting station 50 is shown schematically in FIG. 8, and consists of a turret wheel 150 provided adjacent its periphery with peripherally spaced openings 152 each of which receives a funnel 154. The terminal track portion 12 extends vertically down to the surface of the turret wheel 150 terminating with small clearance over a spot on the wheel that lies on the radius of the funnels 154, so that a seed dropped out of the track 12 will securely fall into the funnel positioned just below. Below the wheel 150 on another wheel 156 supported from wheel 150 by struts 158, a series of vials or receptacles 160 are carried, one associated with and immediately vertically below each funnel 154, so that a seed dropped into a funnel 154 will securely fall into the receptacle 160 just below. A stepper motor 170 mounted on a frame part 172, drives via its output shaft 174 and a conventional coupler 176, the two wheels 150 and 156 in unison or in common. A pin 180 cooperating with a conventional sensor device 182 enables the microprocessor 20 to control the motor and sorting station to home the wheel 150 to ensure that the seeds are dropped into the correct receptacles 160. A photo sensor 184 is associated with each funnel 154 and senses the passage of a seed. In this regard, wherever a photosensor or radiation measurement is to be made, the components of the apparatus surrounding the seed are plastic, such as acrylic.

Figure 2A:
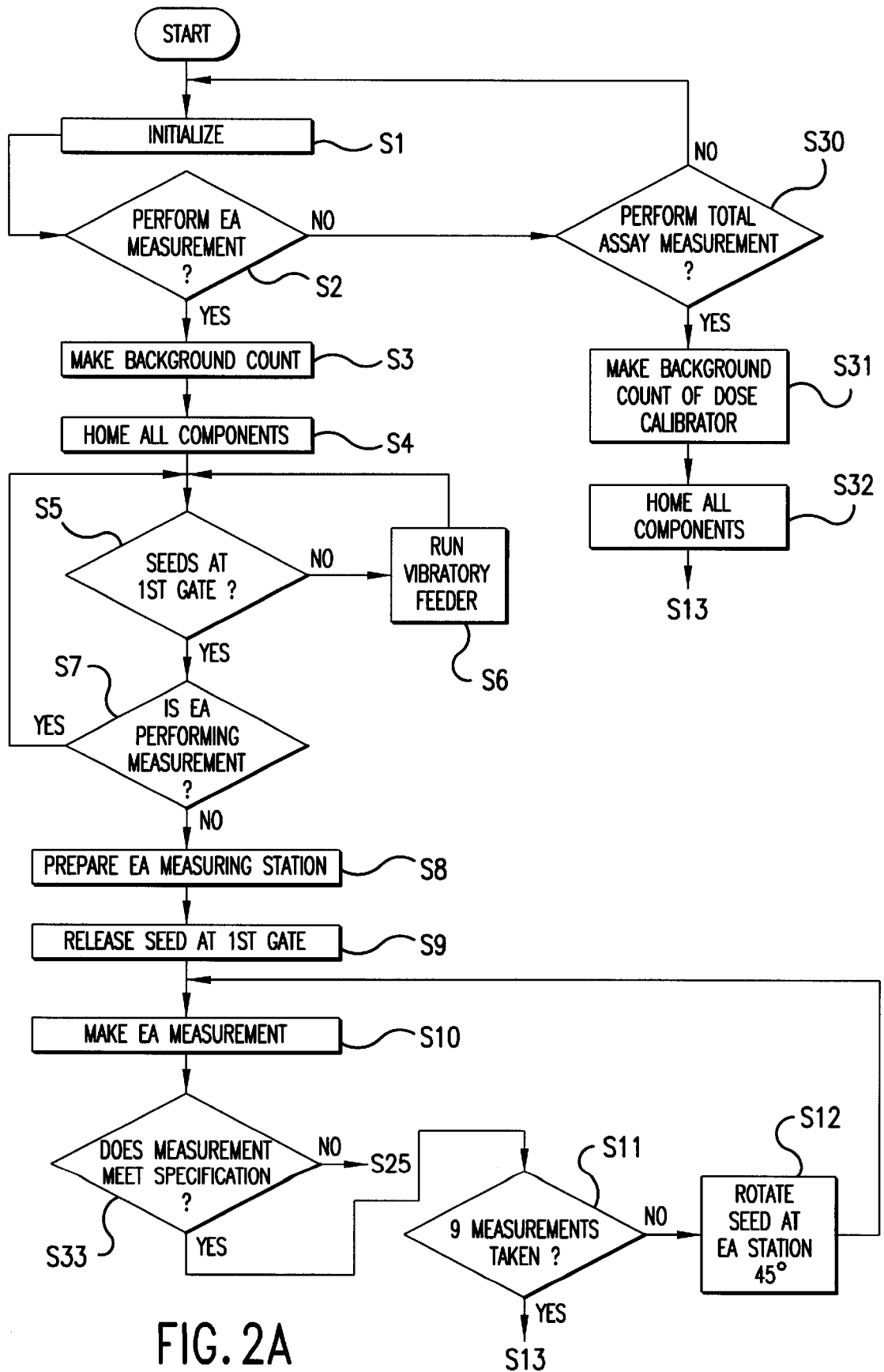
FIGS. 2a and 2b show a flow chart or diagram of the program of the microprocessor.
Figure 2B:
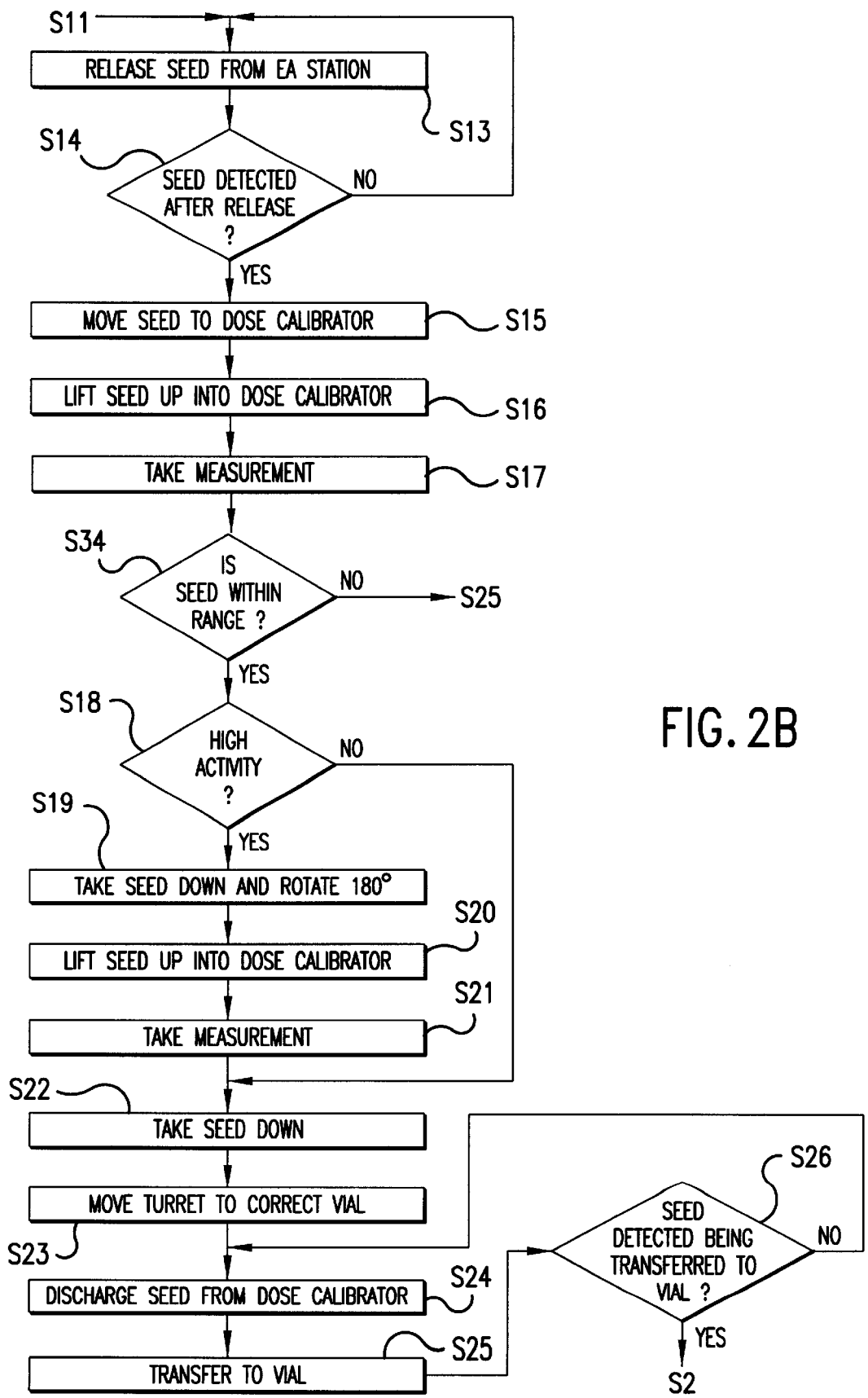

The method of the invention is shown in the flow chart or diagram of FIGS. 2a and 2b. It will be appreciated that the microprocessor is a known general purpose machine which can be suitably programmed to perform the method steps and to control the operation of the apparatus as described herein. Persons of ordinary skill in the art with a knowledge of computers and programming will be able to easily carry out the requisite programming based on the disclosure herein and the flow chart shown in FIGS. 2a and 2b. As shown, the program is started and the first step S1 is to initialize all components. In step S2 a decision is made whether an EA measurement is to be performed. If the answer is N, no, then the program proceeds to step S30 for a decision regarding whether a total assay measurement is to be performed. If the answer is N, no, then the program loops back to step S1. If the answer is Y, yes, the program proceeds to step S31, and a background count of the dose calibrator is made, and to step S32 where all components are homed. The program now jumps to step S13.

If in step S2, the answer is Y, yes, the program advances to step S3 where a background count is made, and to step S4 where all components are homed. Next, in step S5 a decision is made whether seeds are at the first gate. If N, then a command is given to run the vibratory feeder in step S6 and the program loops backs to step S5. If Y, a decision is made whether the EA measuring station is performing a measurement. If Y, the program loop back to step S5. If N, the program proceeds to step S8 where a command is given to prepare the EA measuring station to make a measurement, and the program proceeds to step S9 where a command is given to release a seed at the first gate. In step S10 the command is given to make an EA measurement. The program determines in step S33 if the measurement in step S10 is within or meets the specifications. If N, then the program jumps to step S25 to discard the seed under test directly to a discard vial in the turret wheel, and in the process, all gates are opened so that the seed can be conveyed down the track directly to the vial. If the measurement in step S10 is within or meets the specifications, the decision in step S33 is Y and the program proceeds to step S11. In step 11 a decision is made whether 9 measurements have been taken. If N, a command is given in step S12 to rotate the seed undergoing EA measurement 45 degrees, and the program loops back to step S10. If the answer is Y, the program proceeds to step S13 where a command is given to release the seed from the EA station. If the seed is detected after release (Y) in the decision of step S14, the program proceeds to step S15 where the command is given to move the seed to the dose calibrator station. If no seed is detected (N) in step S14, the program loops back to step S13.

In step S16 the command is given to lift the seed at the dose calibrator station into the dose calibrator. As a predicate to step S16, a decision whether a seed has reached the dose calibrator may be made. In step S17 a command is given to take a measurement of the seed. In step S34 it is determined if the seed is within the radioactivity level for the batch. If N, then the program jumps to step S25. If Y, then the program proceeds to step S18. In step S18 it is determined if the seed has high activity. If Y, then the program proceeds to step S19 where the command is given to take the seed down and rotate the seed 180 degrees, and then, in step S20, the command is given to lift the inverted seed up into the dose calibrator, and in step S21 to take a measurement. In step S22 the command is given to take the seed down. If the decision in step S18 is N, the program jumps to step S22. In step S23 the command is given to move the turret to the correct angular position to place the correct funnel 154 and vial under the exit from track 12. In step S24 the command is given to discharge the seed from the dose calibrator, and in step S25 the command is given to transfer the seed to the selected vial. In step S26 a decision is made whether a seed is detected being transferred to the selected vial. If N, the program loops back to step S24. If Y, the program proceeds to step S2 and is repeated for the next seed. The processing continues until all seeds in a batch have been tested and sorted. If a seed fails a test during the program, commands are given to condition the apparatus to move the seed immediately and directly through the apparatus to a special "discard" vial in the turret or sorting station. Discarded seeds can be placed in a more suitable batch, reprocessed, or discarded totally.

Although the invention has been shown and described in terms of a specific and preferred embodiment, nevertheless, changes and modifications will be evident to those skilled in the art from a knowledge of the teachings herein which do not depart from the spirit or scope of the invention. Such changes and modifications which do not depart from the teachings herein are deemed to fall within the purview of the invention and the concepts taught as expressed in the appended claims.

What is claimed is:

1. A method of assaying and sorting radioactive seeds comprising the steps of:
   a. feeding radioactive seeds single file down a path leading to an activity measuring station,
   b. measuring radioactivity of each seed at the activity measuring station, said measurement being effected by incrementally rotating said seed and measuring radiation emanating from said seed at each incrementally rotated position,
   c. returning measured seeds to the path and moving them further down the path to a sorting station,
   d. establishing at the sorting station a plurality of receptacles to receive and sort the seeds, and controlling the sorting station responsive to the measurements to sort the seeds.

2. The method of claim 1 including the further step of sensing the advance of said seeds.

3. The method of claim 1 wherein step b is carried out by measuring the seed in at least two incrementally rotated positions.

4. The method of claim 1 wherein step b is carried out by rotating the seed about its long axis.

5. The method of claim 4 wherein the seeds are rotated in increments of 45 degrees.

6. The method of claim 1 wherein step b is carried out by pneumatically introducing the seed into a dose calibrator of annular shape.

7. A method of assaying and sorting radioactive seeds comprising the steps of:
   a. storing seeds at a predetermined location,
   b. feeding seeds from said storage in single file to a gated position,
   c. releasing seeds one at a time from the gated position,
   d. advancing each released seed to a first measuring position,
   e. orienting said seed at said first measuring position,
   f. measuring the equatorial anisotropy of said seed by incrementally rotating said seed and measuring radiation emanating from said seed at each incrementally rotated position,
   g. advancing said seed to a second measuring position,
   h. measuring the radiation of said seed by a dose calibrator, and
   i. sorting said seed based on the radiation of said seed and its equatorial anisotropy.

8. The method of claim 7 including the further step of sensing the advance of said seeds.

9. The method of claim 7 wherein step h is repeated with the seed inverted.

10. The method of claim 7 wherein step f is carried out by rotating the seed about its long axis.

11. The method of claim 10 wherein the seeds are rotated in increments of 45 degrees.

12. The method of claim 7 wherein step h is carried out by pneumatically introducing the seed into a dose calibrator of annular shape.

13. Apparatus for assaying and sorting radioactive seeds comprising:
   a. a vibratory feeder,
   b. a track leading from said vibratory feeder,
   c. a measuring station for measuring radioactivity interposed in said track to receive seeds moving down said track and return seeds to said track when measurements of seeds have been completed, said measuring station including a holder to receive seeds serially, a mechanism to incrementally rotate a held seed, and a measuring device to measure radiation emanating from the held seed at each incrementally rotated position,
   d. a sorter having a plurality of receptacles positioned to receive returned seeds from said track, and
   e. a controller to position the sorter responsive to the measurements of the radioactive seeds to effectively sort the seeds into the plurality of receptacles.

14. Apparatus for assaying and sorting radioactive seeds according to claim 13 wherein the sorter includes a turret wheel having a plurality of funnels mounted in a peripherally spaced pattern adjacent its periphery, the plurality of receptacles being mounted beneath the funnels to receive seeds passing through the funnels, and a driver to rotate the turret wheel so that a selected one of the funnels is located vertically below the exit of the track for each exiting seed.

15. Apparatus for assaying and sorting radioactive seeds according to claim 13 wherein sensors sense movement of a seed at preselected points through the apparatus.

16. Apparatus for assaying and sorting radioactive seeds comprising:
   a. a vibratory feeder,
   b. a track leading from said vibratory feeder, c. a first gate interposed in said track, d. an EA measuring station interposed in said track downstream from said first gate including a mechanism to rotate a seed received at said EA station, e. a dose measuring station interposed in said track downstream from said EA station, f. a sorting mechanism containing a plurality of sort receptacles, g. said track terminating in proximity with the sorting mechanism to drop seeds exiting from the track into one of the plurality of receptacles, and h. a controller to control the sorting mechanism to direct seeds into selected ones of said plurality of receptacles in response to measurements obtained at the measuring stations.

17. Apparatus for assaying and sorting radioactive seeds according to claim 16 wherein said first gate comprises a shaft for trapping a seed, and a driver for the shaft to rotate same to release a trapped seed.

18. Apparatus for assaying and sorting radioactive seeds according to claim 16 wherein said EA station includes a cylinder bearing mounted for rotation, a trap carried by said cylinder to trap a seed with its long axis in a preselected orientation, a counter having an elongated window substantially equal to the profile of a trapped seed to read radiation therefrom, and a driver to rotate the cylinder to a plurality of angular positions.

19. Apparatus for assaying and sorting radioactive seeds according to claim 16 wherein the dose measuring station includes a spool mounted for rotation and axial shifting, said spool being mounted in a cylinder and being capable of trapping a seed, a tube communicating with the spool for receiving a trapped seed, a dose calibrator surrounding said tube, and a pneumatic system for moving a seed in said spool up said tube into said dose calibrator and holding it in a measuring position.

20. Apparatus for assaying and sorting radioactive seeds according to claim 16 wherein the sorting mechanism includes a turret wheel having a plurality of funnels mounted in a peripherally spaced pattern adjacent its periphery, a series of receptacles mounted beneath the funnels to receive seeds passing through the funnels, and a driver to rotate the turret wheel so that a selected one of the funnels is located vertically below the exit of the track for each exiting seed.

21. Apparatus for assaying and sorting radioactive seeds according to claim 16 wherein sensors sense movement of a seed at preselected points through the apparatus.

* * * * *